United States Patent [19]

Bruce

[11] 4,277,179
[45] Jul. 7, 1981

[54] RESONANT SUBCAVITY DIFFERENTIAL SPECTROPHONE

[75] Inventor: Charles W. Bruce, Las Cruces, N. Mex.

[73] Assignee: The United States of America as represented by the Secretary of the Army, Washington, D.C.

[21] Appl. No.: 19,688

[22] Filed: Mar. 12, 1979

[51] Int. Cl.³ .................................. G01N 21/59
[52] U.S. Cl. ........................... 356/433; 250/344; 356/439
[58] Field of Search ............ 356/433, 434, 435, 436, 356/437, 439, 440, 410, 409, 411, 441, 442; 250/343, 344, 345, 373, 564, 565; 73/61 R

[56] References Cited

U.S. PATENT DOCUMENTS

| Re. 23,023 | 8/1948 | Wolf et al. ............................. 356/411 |
| 2,019,871 | 11/1935 | Pettingill et al. ..................... 356/411 |
| 2,362,278 | 11/1944 | Jones ........................................ 356/36 |
| 3,111,839 | 11/1963 | Evans et al. ......................... 73/61 R |
| 3,200,700 | 8/1965 | Topol ..................................... 73/61 R |
| 3,238,452 | 3/1966 | Schmitt et al. ....................... 73/61 R |
| 4,058,725 | 11/1977 | Aine ..................................... 250/343 |

OTHER PUBLICATIONS

Bruce et al., "Application of Pulsed-Source Spectrophone to Absorption by Methane at DF Laser Wavelengths," *Applied Optics*, vol. 15, No. 12, Dec. 1976, pp. 2970-2972.

Bruce et al., "In-Situ Measurements of Aerosol Absorption With a Resonant CW Laser Spectrophone," *Applied Optics*, vol. 16, No. 7, Jul. 1977, pp. 1762-1765.

Primary Examiner—R. A. Rosenberger
Attorney, Agent, or Firm—Nathan Edelberg; Jeremiah G. Murray; Bernard Franz

[57] ABSTRACT

The highly sensitive spectrophone assembly of the subject invention simultaneously and continuously provides an accurate measure of the absorption of electromagnetic radiation by atmospheric gases and particulate matter by providing successive flow through chambers. The gases and particulate matter pass through the first chamber, are directed through a filter where the particulate matter is removed, leaving the gases to flow through the second chamber. The signal representative of the absorption of energy is generated in each chamber and fed into a differential amplifier, to provide an accurate indication of the particulate matter in the atmosphere being monitored. Grounding one side yields a signal attributable to the gaseous absorption.

1 Claim, 4 Drawing Figures

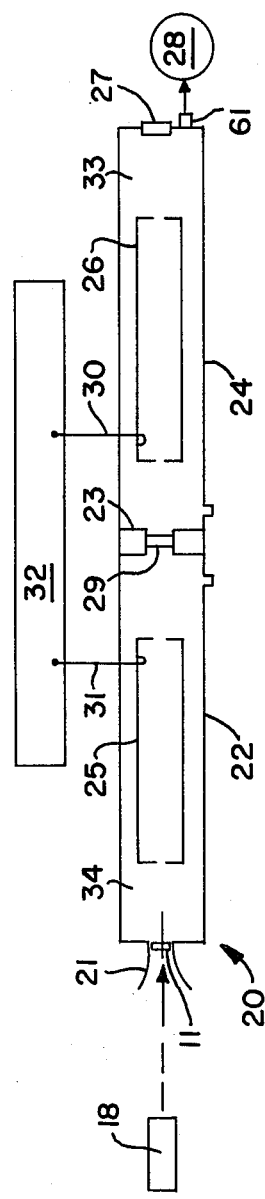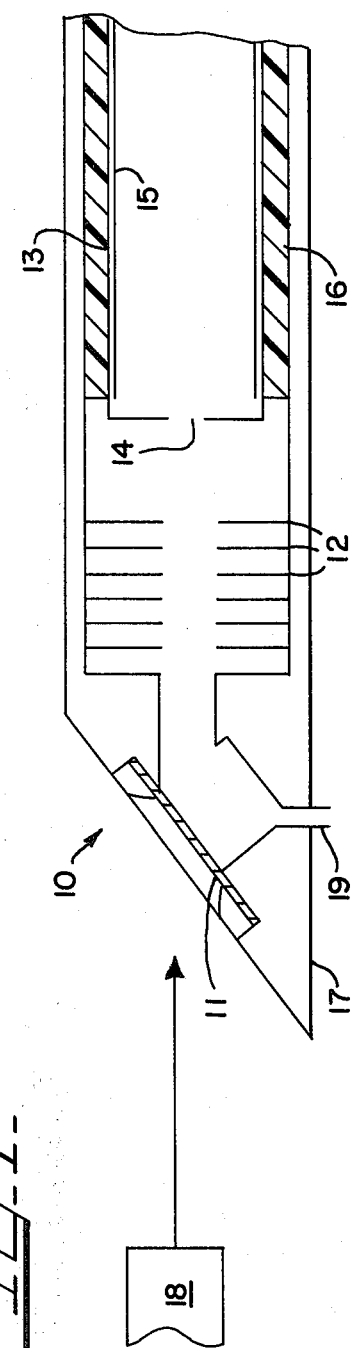

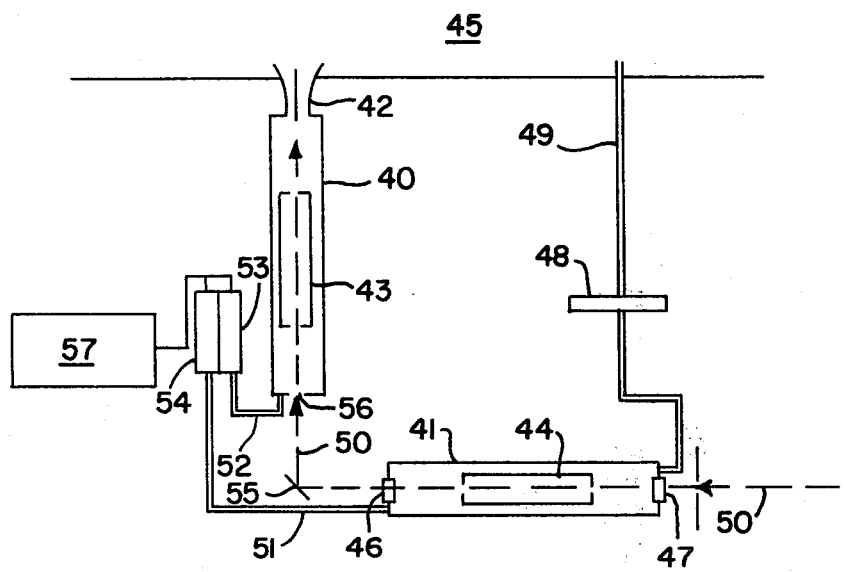
Fig-3-
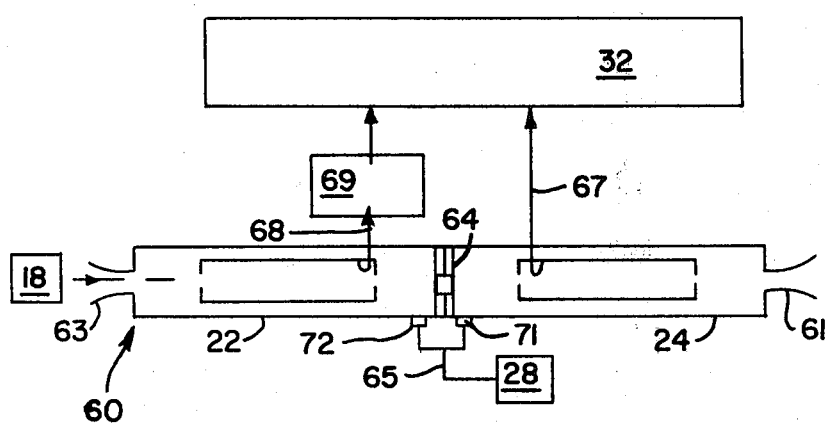
Fig-4-

RESONANT SUBCAVITY DIFFERENTIAL SPECTROPHONE

The invention described herein may be manufactured and used by or for the United States Government for governmental purposes without the payment of any royalties therefor or thereon.

BACKGROUND OF THE INVENTION

The present invention relates to an apparatus for measuring the electromagnetic radiation absorbed by gaseous and particulate matter on exposure to light and, more particularly, to a spectrophone assembly which is capable of simultaneously and accurately measuring individual atmospheric particulate and gaseous radiation absorptions in situ.

The electromagnetic radiation absorption properties of gases and particulate substance have proven increasingly important to such diverse interests as high energy laser propagation, electro-optical sensors, communications by optical systems, the control of atmospheric particulate matter and other radiation absorbing atmospheric pollutants. Since more atmospheric gaseous absorbers are unstable (e.g. ozone and the various nitrogen oxides) and some atmospheric aerosol particulates are known to contain significant amounts of volatile components (and therefore to be rather tenuous in nature) it is desirable to measure their absorption in situ. Measurement of aerosol particulate matter absorption in situ is difficult and has to date only been done definitively by rather indirect techniques. The spectrophone of the subject invention makes the necessary measurements more directly, bypassing altogether the previously required measurements of particle size, shape, and complex refractive index. The principal advantage in utilizing a spectrophone to measure these properties is the potential for higher sensitivity than may be obtained with more traditional comparative path transmission measurements.

The prior art describes a resonant spectrophone which measures radiation absorption by exposing the medium to be tested to a laser beam or other high intensity light source and measuring the energy absorbed by the gaseous or particulate medium in an acoustically tuned absorption chamber using a microphone as an audio sensor. However, the optical energy absorbed by the end windows of the spectrophone chamber produces an undesirable acoustical signal for transmission into the medium being measured. In the past, this spurious signal has rendered highly accurate measurements by spectrophone unattainable and, as a result, it has not been possible to use the spectrophone for a comprehensive analysis of airborne pollution comprising both gaseous and particulate constituents of different absorption properties.

SUMMARY OF THE INVENTION

Therefore, an object of the spectrophone of the subject invention is an apparatus for measuring air pollutants in situ with a high degree of accuracy.

A further object of the present invention is a means of simultaneously and continuously measuring, with high sensitivity, the individual radiation absorption of both gases and particulate substance in situ.

In accordance with the objects of the subject invention, an inventive resonant differential spectrophone is described, having two spectrophones axially joined for air flow from a single source through each spectrophone, with an air filter separating the two spectrophones for trapping and removing particulate matter from the air flow prior to entry to the second spectrophone with a window allowing the passage of light beam from the first chamber to the second chamber. As the air flow passes through each chamber, the absorption of energy by the gases and particulate matter on interaction with the light beam is measured in the first spectrophone chamber and the absorption of the energy by the gases alone is simultaneously measured in the second spectrophone chamber. The resultant signal emanating from each spectrophone is fed into a differential phase lock amplifier. The difference signal of the amplifier may be attributed to the absorption from the particulate matter alone. Grounding the first spectrophone signal yields a measurement attributable to the absorption of energy by the gases of the second spectrophone. With these readings, both the total and individual measurements of all the constituents may be made in a continuous and accurate manner.

The attainment of the above further objects of this invention will be apparent from the following detailed description taken in conjunction with the accompanying drawings forming a part thereof, wherein:

FIG. 1 is a schematic drawing of the resonant subcavity spectrophone used in the instrumental apparatus of the subject invention.

FIG. 2 is a schematic drawing of one embodiment of the Differential Resonant Spectrophone of the subject invention.

FIG. 3 is a schematic drawing of another embodiment of the Differential Resonant Spectrophone of the subject invention.

FIG. 4 is a schematic drawing of the embodiment of FIG. 2 shown converted to a form of equalizing the gain for each spectrophone.

Referring now to FIG. 1, there is shown a portion of a basic spectrophone 10 as is intended for use with the subject invention. The spectrophone 10 comprises an acoustically resonant subcavity or microphone cavity 13 mounted within a larger outer cavity or cell 17. The subcavity or microphone cavity 13 may be held tightly within the outer cell and spaced a desired distance from the outer cell by a Teflon ® sleeve or spacer 16. The user of spacer 16 may be eliminated should the microphone be constructed of stainless steel. An optical window 11 on one end of the cavity 17 allows the passage of light such as a laser beam from source 18 for entrance into the interior chamber 13 along the central axis of the outer cavity 17 (as shown in FIG. 1). The window, generally of barium flouride, may be placed at an angle as shown, for maximum transmission, or it may be orthogonal to the incoming light beam.

A problem has been recognized in the use of spectrophones is that energy absorbed by the window 11 due to the passage of the light is generally transmitted into the medium being measured. In measurements requiring high sensitivity, this window noise can be equal or greater than the measurements desired. To counteract this effect, acoustic dampening discs 12 may be placed within outer cavity 17, clustered about the incoming light path. More importantly, the resonant subcavity 13 in which the desired signal is generated is spaced a short distance from the window 11. Thus, as the light enters the cavity 17 through the window 11, the window noise is dampened and effectively eliminated by the distance traveled between the window and the resonant subcavity 13. While not shown, the rear portion of the spectrophone chamber may be identical to the front portion forming, in effect, a parallelogram with a subcavity 13 spaced from either end.

The acoustic dampening discs 12 may be unnecessary, as the distance between the light and the subcavity 13 has been found sufficient to reduce the window noise to an acceptable level.

A capacitance microphone or sensor 15 is combined inside the resonant subcavity 13. Microphone 15 comprises an aluminum coated MYLAR ® diaphragm in the form of a complete circular cylinder. For resilience, this diaphragm is separated by minute periodic spacers (not shown) from the metallic inner subcavity chamber 13. The electronic signal generated by microphone 15, representative of energy levels within the resonant subcavity 13, is transmitted to a suitable readout device.

Air flow may be provided through the spectrophone as desired, such as being drawn through inlet 19 by a suitable pump 28 (see FIGS. 2 and 4).

In the use of the spectrophone in FIG. 1 in the subject invention, two such spectrophones 22 and 24 may be coupled together in series, or end to end as shown in FIG. 2 to form the combined spectrophone assembly or instrumental apparatus 20 of the subject invention. The outer cavity 34 of one spectrophone 22 is axially aligned and joined with an outer cavity 33 of the other spectrophone 24, with an optical window 29 centered about the axis at the point of joinder of the spectrophones 22 and 24 to permit the passage of the light beam from one unit to the other. A particulate filter 23, shown here as encircling optical window 29, allows the passage of air from one cavity 22 to the second cavity 24, while filtering out the particulate matter in the air flow. Other means of filtering the air flow in its passage through the respective cavities without interference with the light beam are contemplated as within the scope of the subject invention. The air flow is drawn by pump 28 from air inlet horn 21 through the respective cavities 22 and 24.

As described above, the window noise generated by the interaction between the light beam and the window 11 is dampened by the spacing between the subcavity or microphone 25 and the air flow inlet 21. The air flow containing both aerosol particulate matter and gases passes through the first spectrophone 22. The second spectrophone 24 receives only the gaseous constituents of the atmosphere as the particulate matter is filtered out by the passage of the atmospheric medium through filter 23. Thus, as a light beam passes through subcavity or microphone 25, a signal is generated representative of the absorption of optical radiation by both the atmospheric airborne particulates and gases in the atmosphere. The electrical signal generated by the microphone 25 is coupled by lead 31 to a differential phase lock amplifier 32.

The light beam also passes through optical window 29 into cavity 33 and then to subcavity or microphone 26 where the absorption of optical radiation may be attributed solely to the gaseous constituents of the atmosphere. The electrical signal thus generated by microphone 26 is coupled by lead 30 into differential phase lock amplifier 32.

Thus, when a continuous wave or pulsed radiation source such as a laser beam is used, two microphone signals are simultaneously fed into the differential input of phase lock amplifier 32 for combining and differentially comparing the two signals. The gain factor of both microphones 25 and 26 is adjusted to be the same so that the difference in the output signal of the phase lock amplifier is due to the particulate absorption.

The signal due to the gaseous absorption may be found simply by grounding the signal generated by the microphone in resonant subcavity 25 for the combined gaseous and particulate matter of absorption.

The light beam passes out of the instrumental apparatus 20 through optical window 27 for subsequent use and/or absorption as desired.

The apparatus 20 shown in FIG. 2, may be temporarily modified to the apparatus 60 shown in FIG. 4 for purposes of equalizing or adjusting the relative gain of the two spectrophones 22 and 24. To calibrate this form of the invention, the pump 28 is disengaged from port 61 and reattached to each of two ports 71 and 72, located at the junction of the two spectrophones 22 and 24, thereby gaining access to and creating an air flow within each respective cavity 25 and 26 through respective air inlets 61 and 63. The relative gain for spectrophone 22 is then adjusted by a suitable gain equalizing circuit such as amplifier 69 such that the output of the phase lock amplifier 32 is null. A filter 64 is then inserted, and the air flow is switched to series by reconnecting the pump 28 to port 61 and closing port 71 and 72, thereby converting the instrument to that shown in FIG. 2.

An alternative embodiment of the subject invention shown in FIG. 3, demonstrates that the spectrophone of the subject invention may be utilized with a parallel air flow as well as with a series air flow. In this embodiment, air is drawn from the atmospheric medium 45 through inlet 42 for entry into the spectrophone 40 and then into the inner subcavity or microphone 43 for sensing and measuring gas and particulate matter. This spectrophone 40 is in a vertical orientation so that the large particulate matter will not be lost by settling or the like, and may or may not use an optical window at its lower end 56. A pump 57 is connected to drawn air through spectrophone 40 and through a flow meter 53, which is connected by conduit 52 to the spectrophone 40. A second spectrophone 41, for sensing and measuring gas absorption only, draws air from the same atmospheric source through conduit 49. This air flow is cleansed of the particulate matter by filter 48 prior to entry into the spectrophone 41 and resonant subcavity or microphone 44. The air flow is generated by pump 57 which draws the air through conduit 51 and flow meter 54. The air flow through each respective spectrophone 40 and 41 may be adjusted by observation of the air flow rate through the respective air flow meters 53 and 54 and adjustment of the rate accordingly by appropriate valves or the like (not shown). While the air flow is drawn in and equalized for each spectrophone, a light beam 50, such as from a laser, enters the spectrophone 41 through optical window 47 and exits through optical window 46, and is then deflected as by mirror 55 so that its path is directed through spectrophone 40, exiting out air inlet 42. The signals from the two spectrophones 40 and 41 are the processed similarly as for the structure of FIG. 2.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. A spectrophone instrument for the in situ measurement of particulate matter and gaseous energy absorption in an atmospheric medium as an indication of pollution content and the like on a continuous basis, comprising a first and a second spectrophone assembly secured to one another along a common axial line, separated by an optical window, a light path disposed about said common axial line for the travel of a light beam from a laser source through each of said spectrophone assemblies, a first subcavity in said first spectrophone assembly and a second subcavity in said second spectrophone assembly, each of said spectrophone assemblies having an outer chamber which extends substantially beyond the subcavity axially at each end, each of said outer chambers having a window of barium flouride placed at an angle for maximum transmission, acoustic dampening discs within each outer chamber clustered about said light path, each of said subcavities having a microphone comprising a cylindrical diaphragm of aluminized mylar axially aligned therein with spacers for sensing energy absorption means including pump means to provide an air flow path generally about said light path for the flow of said atmospheric medium including filter means encircling said optical window between said first spectrophone assembly and said second spectrophone assembly for removal of the particulate matter, so that the atmospheric medium flow includes said particulate and gaseous matter into said first spectrophone assembly and said first subcavity and gaseous matter only entering said second spectrophone assembly and said second subcavity, whereby said light beam interacts with said particulate and gaseous matter for the abosrption of energy, each of said microphones sensing the absorption of energy and transmitting a signal from each subcavity to a differential input of a phase lock amplifier for combining and comparing said signals for an indication of the concentration of particulate matter in said atmosphere, there being included equalization means to effectively equalize the gain factors for the microphones, and by grouding the signal from the microphone in said first subcavity, obtaining an indication of the concentration of gaseous matter in said atmospheric medium;

wherein said equalization means includes a preamplifier for at least one of the microphones which is calibrated by disengaging and reattaching said pump means to parts of the first and second spectrophone assemblies located adjacent their function to modify the flow of said atmospheric medium to be from the outer ends of both the first and the second spectrophone assemblies and symmetrically through toward the center without using said filter means, and then setting the gain of the preamplifier such that the output of the phase lock amplifier is null.

* * * * *